United States Patent [19]
Behler et al.

[11] Patent Number: 5,854,201
[45] Date of Patent: Dec. 29, 1998

[54] TEXTILE SOFTENERS CONCENTRATES BASED ON PENTAERYTHRITOL OR ESTERS THEREOF CONTAINING QUATERNARY AND NONIONIC EMULSIFIERS

[75] Inventors: Ansgar Behler, Bottrop; Guenther Uphues, Monheim; Bernd Wahle, Kaarst; Peter Waltenberger, Breitscheid; Almud Folge, Hilden, all of Germany

[73] Assignee: Henkel Kommanditgesellschaft auf Aktien, Duesseldorf, Germany

[21] Appl. No.: 817,584

[22] PCT Filed: Oct. 9, 1995

[86] PCT No.: PCT/EP95/03969

§ 371 Date: Jul. 10, 1997

§ 102(e) Date: Jul. 10, 1997

[87] PCT Pub. No.: WO96/12002

PCT Pub. Date: Apr. 25, 1996

[51] Int. Cl.[6] .............................. C11D 1/62; C11D 1/74; C11D 1/835
[52] U.S. Cl. .................. 510/515; 510/276; 510/280; 510/289; 510/308; 510/327; 510/329; 510/330; 510/341; 510/356; 510/405; 510/409; 510/411; 510/413; 510/421; 510/504; 510/524; 510/521; 510/522; 510/527
[58] Field of Search ..................... 510/276, 280, 510/289, 308, 327, 329, 330, 341, 356, 405, 409, 411, 413, 421, 504, 524, 521, 522, 515, 527

[56] References Cited

U.S. PATENT DOCUMENTS

| | | | |
|---|---|---|---|
| 5,292,910 | 3/1994 | Raths et al. | 554/149 |
| 5,505,866 | 4/1996 | Bacon et al. | 252/8.6 |
| 5,545,350 | 8/1996 | Baker et al. | 510/517 |
| 5,593,614 | 1/1997 | Laitem et al. | 510/524 |

FOREIGN PATENT DOCUMENTS

| | | |
|---|---|---|
| 0 243 735 | 11/1987 | European Pat. Off. . |
| 0 494 769 | 7/1992 | European Pat. Off. . |
| 0 530 959 | 3/1993 | European Pat. Off. . |
| 20 52 321 | 4/1972 | Germany . |
| 36 12 479 | 10/1987 | Germany . |
| 40 10 606 | 10/1991 | Germany . |
| 42 32 448 | 3/1994 | Germany . |
| 02 047 362 | 2/1990 | Japan . |
| 1 320 996 | 6/1973 | United Kingdom . |
| WO 91/01295 | 2/1991 | WIPO . |
| WO 92/18593 | 10/1992 | WIPO . |
| WO 93/23510 | 11/1993 | WIPO . |
| WO 94/06900 | 3/1994 | WIPO . |
| WO 95/00614 | 1/1995 | WIPO . |

*Primary Examiner*—Paul Lieberman
*Assistant Examiner*—Charles Boyer
*Attorney, Agent, or Firm*—Ernest G. Szoke; Wayne C. Jaeschke; Real J. Grandmaison

[57] ABSTRACT

The invention relates to textile softener concentrates based on pentaerythritol and/or dipentaerythritol fatty acid partial esters. The dispersibility of such softener concentrates in cold water can be significantly improved by addition of a special emulsifier combination of quaternary ammonium compounds and nonionic compounds. The quaternary ammonium compounds are quaternized alkoxylated alkylamines and/or esterquats. Ethoxylated and/or propoxylated fatty acids or fatty acid esters and end-capped fatty alcohol polyglycol ethers are suitable nonionic emulsifiers.

13 Claims, No Drawings

TEXTILE SOFTENERS CONCENTRATES BASED ON PENTAERYTHRITOL OR ESTERS THEREOF CONTAINING QUATERNARY AND NONIONIC EMULSIFIERS

BACKGROUND OF THE INVENTION

1. Field of the Invention

This invention relates generally to textile treatment compositions and, more particularly, to textile softener concentrates with improved dispersibility in cold water based on pentaerythritol and/or dipentaerythritol fatty acid partial esters and a special emulsifier combination of certain quaternary nitrogen compounds and certain nonionic compounds, to a process for their production and to the use of the emulsifier system.

In the context of the invention, textile softener concentrates are understood to be preparations which may be used both in the textile field for the treatment of yarns, fibers, knitted fabrics, woven fabrics or non-wovens and in the home as aftertreatment preparations for washed textiles.

2. Discussion of the Related Art

Softeners are used in the textile industry and in aftertreatment preparations for washed textiles, for example to produce a pleasant fluffy feel, and to improve the processing properties or even the care of the textiles. Quaternary ammonium compounds are normally used as softeners because they are absorbed particularly easily by textiles. One example of such quaternary ammonium compounds are quaternized difatty acid alkanol-amine esters, so-called esterquats, which unfortunately dissolve or disperse inadequately in cold water in relatively high concentrations so that, for example, even the production of aqueous concentrates with an esterquat content of less than 30% by weight is difficult. Dispersibility in cold water can be improved by addition of small quantities of carboxylic acid esters (DE-A-36 12 479) or by addition of fatty alcohols, fatty alcohol polyglycol ethers or polyol fatty acid partial esters (DE-A-42 32 448).

Esters of pentaerythritol and/or dipentaerythritol have recently been proposed as softeners instead of esterquats or other quaternary ammonium compounds. For example, EP-A-494 769 describes water-containing textile softeners which contain pentaerythritol distearate in particular as the principal softener component. However, small quantities of quaternary ammonium compounds, such as esterquats, as softeners are acceptable. To obtain aqueous emulsions with an active content of pentaerythritol esters of 1 to 25%, EP-A-494 769 recommends the addition of emulsifiers, such as higher alkyl dialkanol-amines and/or alkyl polyethylene glycol ethers. Although these emulsifiers are capable of stabilizing lower concentrates with an active content of pentaerythritol esters of 1 to 25%, they lose efficiency in higher concentrates. With the assistance of these emulsifiers, the water-free pentaerythritol/emulsifier mixtures show poor dispersibility in cold water with the result that dispersion in cold water is extremely difficult.

On account of these difficulties, the user would prefer the manufacturer to disperse the concentrate in water although this would involve the storage and transport of considerable quantities of water and, accordingly, would make little sense from the economic point of view.

Accordingly, the problem addressed by the present invention was to provide emulsifiers for softener concentrates which, on the one hand, would enable textile softener concentrates with a high content of pentaerythritol esters to be dispersed in cold water, but which on the other hand would not affect the softening performance of the pentaerythritol esters. Finally, the softener concentrates as a whole would be able to produce the same softness as the quaternary ammonium compounds known as very good softeners from the prior art.

DESCRIPTION OF THE INVENTION

Surprisingly, the problem stated above has been solved by a special emulsifier combination of a quaternary ammonium compound selected from the group of quaternized alkoxylated alkylamines and esterquats and a nonionic compound selected from the group of ethoxylated and/or propoxylated fatty acids or fatty acid esters and end-capped fatty alcohol polyglycol ethers.

Accordingly, the present invention relates to textile softener concentrates with improved dispersibilty in cold water based on pentaerythritol and/or dipentaerythritol fatty acid partial esters as softeners, characterized in that they additionally contain an emulsifier combination of a) a quaternary nitrogen compound selected from the group of a1) quaternized alkoxylated alkylamines corresponding to formula (I):

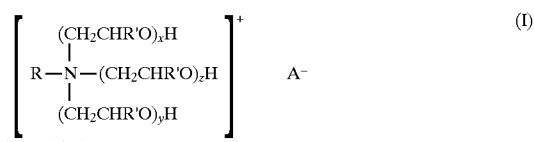

in which
R is an aliphatic hydrocarbon radical containing 6 to 22 carbon atoms,
R' is H or $CH_3$,
x, y, and z independently of one another represent a number of 1 to 20, the sum of x+y+z being $\geq 3$,
A is an anion, a2) quaternized fatty acid alkanolamine esters corresponding to general formula (II):

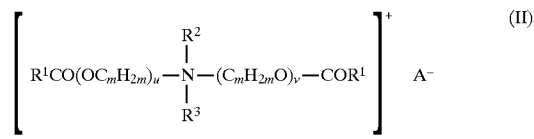

in which $R^1CO$ is a saturated or unsaturated acyl group containing 12 to 22 carbon atoms, $R^2$ is a group $R^1CO(OC_mH_{2m})_w$, an alkyl group containing 1 to 4 carbon atoms or a hydroxyalkyl group containing 2 to 4 carbon atoms and $R^3$ is an alkyl group containing 1 to 4 carbon atoms or a hydroxyalkyl group containing 2 to 4 carbon atoms, m is the number 2 or 3, u, v and w are each a number of 1 to 4 and A- is an anion, and b) a nonionic emulsifier selected from the group of b1) ethoxylated and/or propoxylated fatty acids or fatty acid esters corresponding to formula (III):

in which
$R^5CO$ is an aliphatic acyl radical containing 6 to 22 carbon atoms,
n and o independently of one another represent a number of 0 to 20, the sum of n+o being $\geq 1$, $R^4$ is H or an aliphatic hydrocarbon radical containing 1 to 12 carbon atoms, b2) end-capped fatty alcohol polyglycol ethers corresponding to general formula (IV):

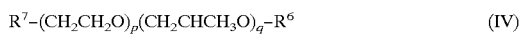

$$R^7-(CH_2CH_2O)_p(CH_2CHCH_3O)_q-R^6 \qquad (IV)$$

in which $R^7$ is an aliphatic hydrocarbon radical containing 6 to 22 carbon atoms, p and q independently of one another are numbers of of 0 to 20, the sum of p+q being $\geq 2$, $R^6$ is an aliphatic hydrocarbon radical containing 1 to 12 carbon atoms.

The quaternized alkoxylated alkylamines corresponding to formula (I) are known compounds which may be prepared, for example, in accordance with DE-A-20 52 321 by ethoxylation of the corresponding alkylamines in the presence of water and subsequent neutralization. The products are obtained in the form of low-viscosity aqueous solutions. Aqueous solutions of the quaternized alkoxylated alkylamines of formula (I) with an active substance content of 40 to 60% by weight are preferably used. The aqueous solutions are preferably adjusted to a pH value of 6 to 8.

If phosphoric acid is used for the neutralization step, A⁻ in formula (I) is a corresponding equivalent of the phosphate. In view of the pH value adjusted, it may be assumed that the anion is $H_2PO_4^-$ and/or $HPO_4^{2-}$.

Within the group of quaternized alkoxylated alkylamines corresponding to formula (I), those in which R is an aliphatic hydrocarbon radical containing 12 to 22 carbon atoms and x, y and z independently of one another are numbers of 1 to 10, the sum of x+y+z being from 3 to 10, are preferred. The quaternized ethoxylated alkylamines (R'=H) are particularly suitable.

The quaternized fatty acid alkanolamine esters corresponding to general formula (II) are also known compounds which may be obtained by the relevant methods of preparative chemistry. One process for their production is described in WO 91/01295, according to which fatty acids are reacted with triethanolamine in the presence of reducing agents, air being passed through the reaction mixture, and the diesters obtained are subsequently quaternized with alkylating agents, such as dimethyl sulfate, dimethyl phosphate or methyl halide. Since the products obtained are technical products, the esterquats of general formula (II) are always mixtures of quaternized mono-, di- and triesters.

If desired, the esterquats may be used in the form of organic solutions, for example in a branched lower alcohol, such as isopropanol.

Quaternized fatty acid alkanolamine esters corresponding to general formula (II), in which $R^1CO$ is an acyl group derived from pure fatty acids or technical mixtures of fatty acids, such as lauric, myristic, palmitic, stearic, oleic, elaidic, petroselic, linoleic, linolenic, arachic, behenic and/or erucic acid, are preferred for the purposes of the invention. In a particularly prefer- red embodiment, $R^1Co$ in formula (II) is a saturated acyl group containing 16 and/or 18 carbon atoms, $R^3$ is a methyl group, m is the number 2, u, v and w are each the number 1 and A is a halide, methosulfate or methophosphate.

Ethoxylated and/or propoxylated fatty acids or fatty acid esters are also known compounds which may be obtained by ethoxylation and/or propoxylation of the fatty acids or fatty acid esters in the presence of catalysts. DE-A-40 10 606 describes a process in which narrow-range ethoxylated and/or propoxylated fatty acid esters are obtained providing hydrophobicized hydrotalcites are used as catalysts.

However, it is also quite possible initially to prepare ethoxylated and/or propoxylated alcohols and then to esterify them with fatty acids.

The products are obtained in liquid or solid form, depending upon the number of carbon atoms in the alcohol and fatty acid components and upon the degree of alkoxylation.

Within this group, the pure ethoxylates (o=0) are particularly preferred. Among the pure ethoxylates, those in which $R^5CO$ in formula (III) is an aliphatic acyl radical containing 12 to 22 carbon atoms, R4 is H or an alkyl group containing 1 to 4 carbon atoms, n is a number of 5 to 15 and o is the number 0 are particularly prefer- red.

Examples of fatty acids from which $R^5CO$ may be derived have been described in connection with the esterquats corresponding to formula (II).

The end-capped fatty alcohol polyglycol ethers corresponding to general formula (IV) are also a known class of compounds which may be obtained by relevant methods of organic chemistry, for example by reaction of alkyl halides with ethoxylated and/or propoxylated fatty alcohols in the presence of a catalyst.

Those compounds of formula (IV) in which $R^7$ is an aliphatic hydrocarbon radical containing 12 to 22 carbon atoms, p is a number of 2 to 8, q is a number of 0 to 5 and $R^6$ is an alkyl radical containing 1 to 4 carbon atoms are preferred for the purposes of the invention. $R^7$ may be derived from pure fatty alcohols or technical mixtures of fatty alcohols, such as lauryl, myristyl, palmityl, stearyl, arachidyl, behenyl, oleyl, elaidyl, linoleyl and/or linolenyl alcohol.

The textile softener concentrates according to the invention contain pentaerythritol and/or dipentaerythritol fatty acid partial esters as the principal component actually responsible for softness. Corresponding pentaerythritol and/or dipentaerythritol fatty acid partial esters are described in detail for this application in EP-A-0 494 769 which has already cited. The pentaerythritol and dipentaerythritol fatty acid partial esters described therein are included in the disclosure of the present application. Within this group, pentaerythritol difatty acid esters of $C_{16-22}$ fatty acids are particularly preferred, pure or technical pentaerythritol distearate being most particularly preferred.

To improve the dispersibility of the softener concentrates in cold water, an emulsifier combination of the described type is added to the pentaerythritol and/or dipentaerythritol fatty acid partial esters.

It has proved to be of advantage to add the nonionic emulsifiers described under b) in at least the same ratio by weight as, but preferably in larger quantities than, the quaternary nitrogen compounds. Preferred ratios by weight of nonionic emulsifiers to quaternary nitrogen compounds are 1:1 to 3:1 and preferably 1.5:1 to 2:1.

The softener concentrates according to the invention preferably contain 70 to 95% by weight of pentaerythritol and/ordipentaerythritol fatty acid partial esters, 5 to 30% by weight of the described emulsifier combinations and 0 to 20% by weight of typical auxiliaries.

Typical auxiliaries are, for example, pH regulators, such as organic and inorganic acids, foam inhibitors, viscosity regulators, antioxidants, dyes, fragrances and soil release agents. The softener concentrates according to the invention advantageously do not contain additional water because high contents of active substances are required. However, the concentrates may of course contain some water introduced, for example, by the active substances and auxiliaries used in the production process, for example by addition of hydrochloric acid (auxiliary) or where the compounds of formula (I) are added in the form of an aqueous solution. The quantities of water thus introduced are included among the 0 to 20% by weight of auxiliaries.

The softener concentrates according to the invention are distinguished by good dispersibility in cold water. In addition, the incorporation of the described emulsifier combination does not affect the performance of the pentaerythritol and/or dipentaerythritol fatty acid partial esters so that, overall, the softness obtained in practice is comparable with that of dimethyl distearylammonium chloride known as an outstanding softener.

For application, the softener concentrates according to the invention may be diluted with water to the required concentration. Typical concentrations for domes- tic fabric softeners are 3 to 6%. However, higher concentrates containing 10 to 30% of textile softening agents may also be produced and correspondingly smaller quantities added to the final rinse.

After dilution with water to the usual concentrations, the softener concentrates according to the invention may also be used in the textile industry because they are easy to apply by standard methods, such as extraction, dip-extraction, padding or spraying.

The present invention also relates to a process for the production of textile softener concentrates, characterized in that pentaerythritol and/or dipentaerythritol fatty acid partial esters as softeners are first melted and an emulsifier combination according to claim 1 is then added.

According to the invention, the order in which the quaternary nitrogen compounds and nonionic emulsifiers are added is of no significance.

The products obtained may be made up in the usual way, for example by spray crystallization or roll granulation.

The present invention also relates to the use of a combination of
a) a quaternary nitrogen compound selected from the group of
a1) quaternized alkoxylated alkylamines corresponding to formula (I):

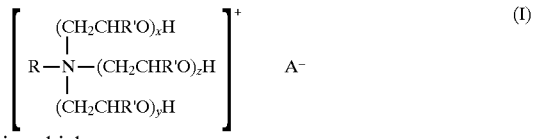

in which
R is an aliphatic hydrocarbon radical containing 6 to 22 carbon atoms,
R' is H or $CH_3$, x, y, and z independently of one another represent a number of 1 to 20, the sum of x+y+z being $\geq 3$,
$A^-$ is an anion,
a2) quaternized fatty acid alkanolamine esters corresponding to general formula (II):

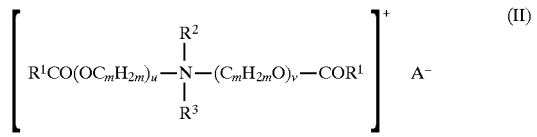

in which $R^1Co$ is a saturated or unsaturated acyl group containing 12 to 22 carbon atoms, $R^2$ is a group $R^1CO(OC_mH_{2m})_w$, an alkyl group containing 1 to 4 carbon atoms or a hydroxyalkyl group containing 2 to 4 carbon atoms and $R^3$ is an alkyl group containing 1 to 4 carbon atoms or a hydroxyalkyl group containing 2 to 4 carbon atoms, m is the number 2 or 3, u, v and w are each a number of 1 to 4 and $A^1$ is an anion, and b) a nonionic emulsifier selected from the group of
b1) ethoxylated and/or propoxylated fatty acids or fatty acid esters corresponding to formula (III):

in which
$R^5CO$ is an aliphatic acyl radical containing 6 to 22 carbon atoms,
n and o independently of one another represent a number of 0 to 20, the sum of n+o being >1,
$R^4$ is H or an aliphatic hydrocarbon radical containing 1 to 12 carbon atoms, b2) end-capped fatty alcohol polyglycol ethers corresponding to general formula (IV):

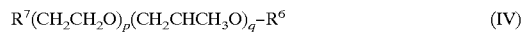

in which
$R^7$ is an aliphatic hydrocarbon radical containing 6 to 22 carbon atoms,
p and q independently of one another are numbers of of 0 to 20, the sum of p+q being $\geq 2$,
$R^6$ is an aliphatic hydrocarbon radical containing 1 to 12 carbon atoms,
as emulsifiers for improving the dispersibility of pentaerythritol and/or dipentaerythritol fatty acid partial esters in cold water.

Relevant particulars can be found in the foregoing disclosure.

EXAMPLES

A) Production of the softener concentrates

1)

50 g of technical pentaerythritol distearate were melted and 8.0 g of an approximately 50% by weight aqueous solution of the phosphoric acid salt of quaternized tallow amine ethoxylated with 10 moles of EO and 12.0 g of an approximately 30% by weight aqueous solution of lauric acid methyl ester ethoxylated with 12 moles of ethylene oxide and also 2.2 g of an approximately 37% hydrochloric acid were added to the resulting melt with stirring at 60° C. The product was converted into flakes on a cooling roller.

A2

50 g of technical pentaerythritol distearate were melted and 8.0 g of an approximately 90% by weight solution of methyl-N,N-bis-(acyloxyethyl)-N-(2-hydroxy- ethyl)-ammonium methosulfate in isopropanol and 12 g of an approximately 30% by weight aqueous solution of lauric acid methyl ester ethoxylated with 12 moles of ethylene oxide were added to the resulting melt with stirring at 60° C. The product was converted into flakes on a cooling roller.

Comparison Example C1

63.5 g of technical pentaerythritol distearate were melted and 10.4 g of a tallow amine ethoxylated with 2 moles of ethylene oxide, 15.0 g of a technical $C_{10-18}$ fatty alcohol mixture (chain distribution: $C_{10}$ 0–2%, $C_{12}$ 70–75%, $C_{14}$ 25–30%, $C_{16}$ 0–2%, $C_{18}$ 0–1%) ethoxylated with 2 moles of ethylene oxide and 2.8 g of an approximately 37% hydrochloric acid were added to the resulting melt with stirring at 60° C. The product was converted into flakes on a cooling roller.

B) Testing of solubility/dispersibility in cold water

Method: 95 g of water were initially introduced and 5 5 g of flakes were added with stirring. Dispersibility in cold water was tested after stirring for another 10 minutes. The quality of the dispersion was then evaluated after 16 hours with no further stirring.

Results:

| Example | Stirring for 10 mins. | Standing for 16 h |
| --- | --- | --- |
| A1 | Flakes largely dissolved; fine-particle dispersion | Completely dissolved; fine-particle dispersion |
| A2 | Flakes largely dissolved; fine-particle dispersion | Completely dissolved; fine-particle dispersion |
| C1 | Flakes only partly swollen; no dispersion | Flakes heavily swollen; only partly dispersed |

These results show that the softener concentrates according to the invention can be dispersed relatively quickly in water with or without stirring.

C) softening performance Test procedure:

An approximately 25×15 cm test specimen of cotton terry was weighed. The treatment liquor was then prepared with tap water at 20° C. in a 1 liter glass beaker.

A liquor ratio (weight of test specimen to liquor volume) of 1:20 was selected. Based on the weight of the test specimen, 0.5% active substance of the substance to be tested was dispersed in the liquor. The test specimen was then gently moved around in the liquor for 5 minutes, for example with a stirring rod. The test specimen was then wrung out and dried in air for 24 hours (washing line). The test specimen should be turned through 180° four times in the first 2 hours to avoid one-sided over-concentrations.

Evaluation:

Fresh standard tests was must always be included for the evaluation of softness. The evaluation itself was a subjective (haptic) test in which at least four people handle the test fabric and award scores on a scale of 0 to 6. A score of 0 represents the feel impression of the water standard, i.e. liquor without active substance, and is synonymous with the worst feel. The better the feel, the higher the scores, a score of 6 being very good. The result represents the average of the evaluations of all test personnel.

Results:

| Example | Evaluation |
| --- | --- |
| A1 | 5.8 |
| A2 | 5.7 |
| C1 | 5.6 |
| Dimethyl distearylammonium chloride (standard) | 5.5 |

(0=very poor, 6=very good)

What is claimed is:

1. A textile softener concentrate having improved dispersibility in cold water comprising
   a) 70% to 95% by weight of pentaerythritol fatty acid partial ester or dipentaerythritol fatty acid partial ester, and
   b) 5% to 30% by weight of an emulsifier component comprising a mixture of
      b1) a quaternary nitrogen compound selected from the group consisting of
         b1i) quaternized alkoxylated alkylamines corresponding to formula (I): Preliminary Amendment of U.S. National Stage for International Application

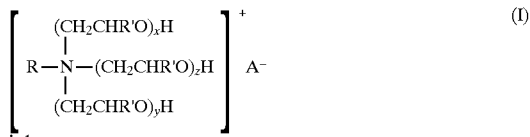

in which
   R is an aliphatic hydrocarbon radical containing 6 to 22 carbon atoms,
   R' is H or $CH_3$,
   x, y, and z independently of one another represent a number of 1 to 20, the sum of x+y+z being $\geq 3$,
   $A^-$ is an anion, and
   b1ii) quaternized fatty acid alkanolamine esters corresponding to formula (II):

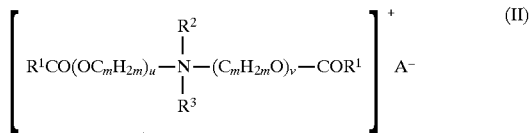

in which $R^1CO$ is a saturated or unsaturated acyl group containing 12 to 22 carbon atoms, $R^2$ is a group $R^1CO(OC_mH_{2m})_w$, an alkyl group containing 1 to 4 carbon atoms or a hydroxyalkyl group containing 2 to 4 carbon atoms and $R^3$ is an alkyl group containing 1 to 4 carbon atoms or a hydroxyalkyl group containing 2 to 4 carbon atoms, m is the number 2 or 3, u, v and w are each a number of 1 to 4 and A- is an anion, and
   b2) a nonionic emulsifier selected from the group consisting of
      b2i) ethoxylated or propoxylated fatty acids or fatty acid esters corresponding to formula (III):

in which
   $R^5CO$ is an aliphatic acyl radical containing 6 to 22 carbon atoms,
   n and o independently of one another represent a number of 0 to 20, the sum of n+o being $\geq 1$,
   $R^4$ is H or an aliphatic hydrocarbon radical containing 1 to 12 carbon atoms, and
   b2ii) end-capped fatty alcohol polyglycol ethers corresponding to formula (IV):

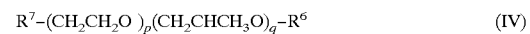

in which
   $R^7$ is an aliphatic hydrocarbon radical containing 6 to 22 carbon atoms,
   p and q independently of one another are numbers of 0 to 20, the sum of p+q being $\geq 2$, and
   $R^6$ is an aliphatic hydrocarbon radical containing 1 to 12 carbon atoms.

2. A textile softener concentrate as in claim 1 wherein said anion A- in formula (I) stands for a corresponding equivalent of the phosphate and, in formula (II), for a halide, methosulfate or methophosphate.

3. A textile softener concentrate as in claim 1 wherein said nonionic emulsifier is an ethoxylated or propoxylated fatty acid, $R^5CO$ in formula (III) is an aliphatic acyl radical containing 12 to 22 carbon atoms, n is a number of 5 to 15, o is the number 0, and $R^4$ is H or an alkyl radical containing 1 to 4 carbon atoms.

4. A textile softener concentrate as in claim 1 wherein said nonionic emulsifier is an end-capped fatty alcohol polyglycol ether, $R^7$ in formula (IV) is an aliphatic hydrocarbon radical containing 12 to 22 carbon atoms, p is a number of 2 to 8, q is a number of 0 to 5 and $R^6$ is an alkyl radical containing 1 to 4 carbon atoms.

5. A textile softener concentrate as in claim 1 wherein said emulsifier mixture contains said nonionic emulsifier in a ratio by weight to said quaternary nitrogen compound of 1:1 to 3:1.

6. A textile softener concentrate as in claim 1 wherein said dipentaerythritol fatty acid partial ester comprises pentaerythritol difatty acid esters of fatty acids containing 16 to 22 carbon atoms.

7. A textile softener concentrate as in claim 1 free of water.

8. The process of producing a textile softener concentrate having improved dispersibility in cold water comprising melting
a) 70% to 95% by weight of pentaerythritol or dipentaerythritol fatty acid partial ester, and adding thereto
b) 5% to 30% by weight of an emulsifier component comprising a mixture of
b1) a quaternary nitrogen compound selected from the group consisting of
b1i) quaternized alkoxylated alkylamines corresponding to formula (I):

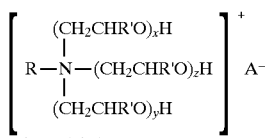

in which
R is an aliphatic hydrocarbon radical containing 6 to 22 carbon atoms,
R' is H or $CH_3$,
x, y, and z independently of one another represent a number of 1 to 20, the sum of x+y+z being $\geq 3$,
$A^-$ is an anion, and
b1ii) quaternized fatty acid alkanolamine esters corresponding to formula (II):

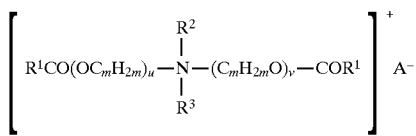

in which R° CO is a saturated or unsaturated acyl group containing 12 to 22 carbon atoms, $R^2$ is a group $R^1CO(OC_mH_{2m})_w$, an alkyl group containing 1 to 4 carbon atoms or a hydroxyalkyl group containing 2 to 4 carbon atoms and $R^3$ is an alkyl group containing 1 to 4 carbon atoms or a hydroxyalkyl group containing 2 to 4 carbon atoms, m is the number 2 or 3, u, v and w are each a number of 1 to 4 and A- is an anion, and
b2) a nonionic emulsifier selected from the group consisting of
b2i) ethoxylated or propoxylated fatty acids or fatty acid esters corresponding to formula (III):

in which
$R^5CO$ is an aliphatic acyl radical containing 6 to 22 carbon atoms,
n and o independently of one another represent a number of 0 to 20, the sum of n+o being 2 1,
$R^4$ is H or an aliphatic hydrocarbon radical containing 1 to 12 carbon atoms, and
b2ii) end-capped fatty alcohol polyglycol ethers corresponding to formula (IV):

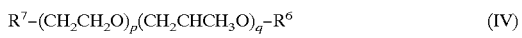

in which
$R^7$ is an aliphatic hydrocarbon radical containing 6 to 22 carbon atoms,
p and q independently of one another are numbers of 0 to 20, the sum of p+q being $\geq 2$, and
$R^6$ is an aliphatic hydrocarbon radical containing 1 to 12 carbon atoms.

9. A process as in claim 8 wherein said anion $A^-$ in formula (I) stands for a corresponding equivalent of the phosphate and, in formula (II), for a halide, methosulfate or methophosphate.

10. A process as in claim 8 wherein said nonionic emulsifier is an ethoxylated or propoxylated fatty acid, $R^5CO$ in formula (III) is an aliphatic acyl radical containing 12 to 22 carbon atoms, n is a number of 5 to 15, o is the number 0, and $R^4$ is H or an alkyl radical containing 1 to 4 carbon atoms.

11. A process as in claim 8 wherein said nonionic emulsifier is an end-capped fatty alcohol polyglycol ether, $R^7$ in formula (IV) is an aliphatic hydrocarbon radical containing 12 to 22 carbon atoms, p is a number of 2 to 8, q is a number of 0 to 5 and $R^6$ is an alkyl radical containing 1 to 4 carbon atoms.

12. A process as in claim 8 wherein said emulsifier mixture contains said nonionic emulsifier in a ratio by weight to said quaternary nitrogen compound of 1:1 to 3:1.

13. A process as in claim 8 wherein said dipentaerythritol fatty acid partial ester comprises pentaerythritol difatty acid esters of fatty acids containing 16 to 22 carbon atoms.

* * * * *